US00PP19781P2

(12) United States Plant Patent
Danziger

(10) Patent No.: US PP19,781 P2
(45) Date of Patent: Mar. 3, 2009

(54) ***IMPATIENS* PLANT NAMES 'DANMU24'**

(50) Latin Name: *Impatiens walleriana*
Varietal Denomination: DANMU24

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,645

(22) Filed: Jan. 11, 2008

(51) Int. Cl.
*A01H 5/00* (2006.01)

(52) U.S. Cl. ..... Plt./319

(58) Field of Classification Search ..... Plt./319
See application file for complete search history.

*Primary Examiner*—Annette H Para
*Assistant Examiner*—S. B. McCormick-Ewoldt

(57) ABSTRACT

A new and distinct *Impatiens* cultivar named 'DANMU24' is disclosed, characterized by having a compact, free-branching, upright and rounded plant habit, distinctive double salmon colored flowers, and small foliage. The new variety is an *Impatiens,* normally produced as an outdoor garden or container plant.

2 Drawing Sheets

Latin name of the genus and species: *Impatiens walleriana.*

Variety denomination: 'DANMU24'.

BACKGROUND OF THE INVENTION

The new cultivar is a product of a planned breeding program, under the direction of the inventor, Gabriel Danziger. The objective of the breeding program was to produce plants of *Impatiens walleriana* with compact growth habits and double flowers. The seed parent is the unpatented, proprietary seedling variety referred to as *Impatiens walleriana* '183HF.' The pollen parent is the unpatented, proprietary seedling variety referred to as *Impatiens walleriana* '248HF.' The new variety was discovered in June 2006, by the inventor in a group of seedlings resulting from that crossing, in Moshav Mishmar Hashiva, Israel.

Asexual reproduction of the new cultivar 'DANMU24' by vegetative cuttings was first performed at a commercial greenhouse in Moshav Mishmar Hashiva, Israel in June 2006. Subsequent reproduction has shown that the unique features of this cultivar are stable and reproduced true to type on successive generations.

SUMMARY OF THE INVENTION

The cultivar 'DANMU24' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANMU24' These characteristics in combination distinguish 'DANMU24' as a new and distinct *Impatiens* cultivar:

1. Compact plant habit.
2. Small leaves compared to other commercial *Impatiens* varieties.
3. Distinctive salmon flower color.
4. Upright and rounded plant habit.
5. Free branching habit.
6. Double flowering habit.

Plants of the new cultivar 'DANMU24' are similar to plants of the seed parent, *Impatiens walleriana* '183HF' in most horticultural characteristics, including plant habit and flower color. however, plants of the new cultivar 'DANMU24' produce a double flower, whereas '183HF' produces a single flower.

Plants of the new cultivar 'DANMU24' are similar to plants of the pollen parent, *Impatiens walleriana* '248HF' in most horticultural characteristics, including plant habit and flower color. However, plants of the new cultivar 'DANMU24' produce a double flower, whereas '248HF' produces a single flower.

COMMERCIAL COMPARISON

Plants of 'DANMU24' can be compared to the commercial variety 'BALOLESAL' U.S. Plant Pat. No. 13,648. However, plants of 'DANMU24' are more compact and produce smaller leaves than the comparison variety. Plants of 'DANMU24' grown under comparable conditions to 'BALOLESAL' reach a width of 30 cm, compared to 40 cm of 'BALOLESAL'

BRIEF DESCRIPTION OF THE PHOTOGRAPH

Figure 1:
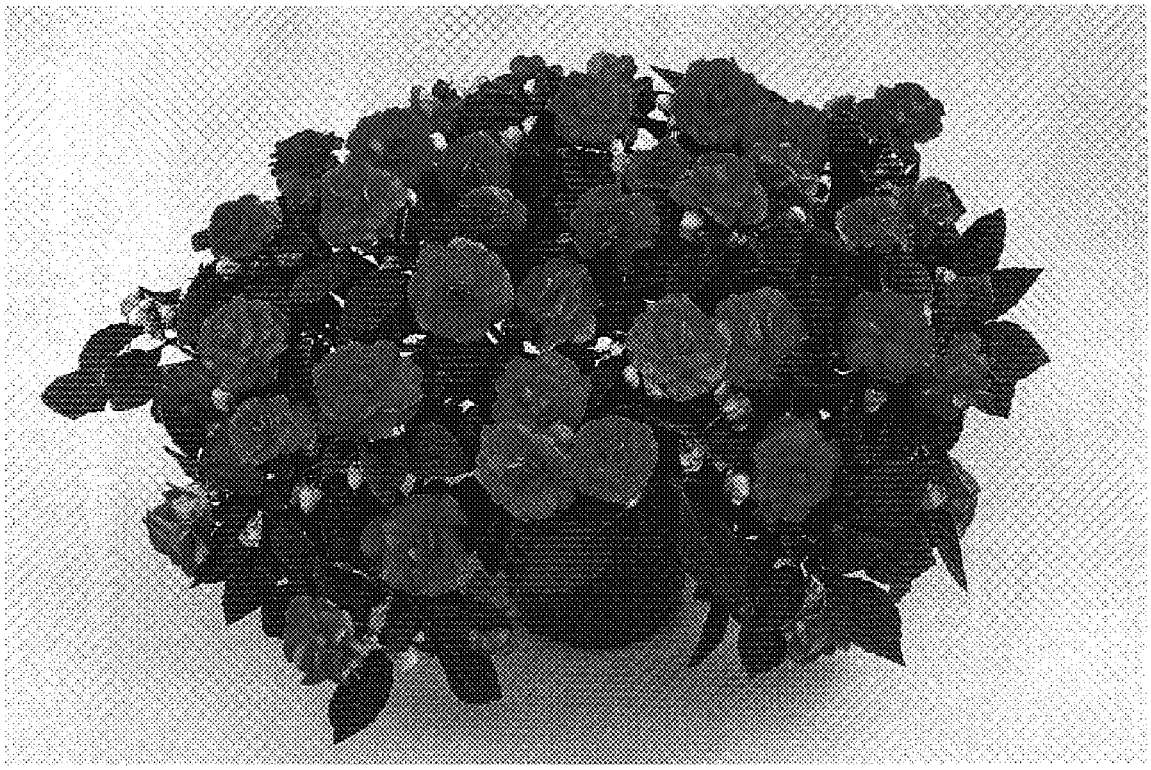

The accompanying photograph in FIG. 1 illustrates in full color a typical plant of 'DANMU24' grown in a greenhouse, in a 16 cm pot. Age of the plant photographed is approximately 3 months from a rooted cutting.

Figure 2:
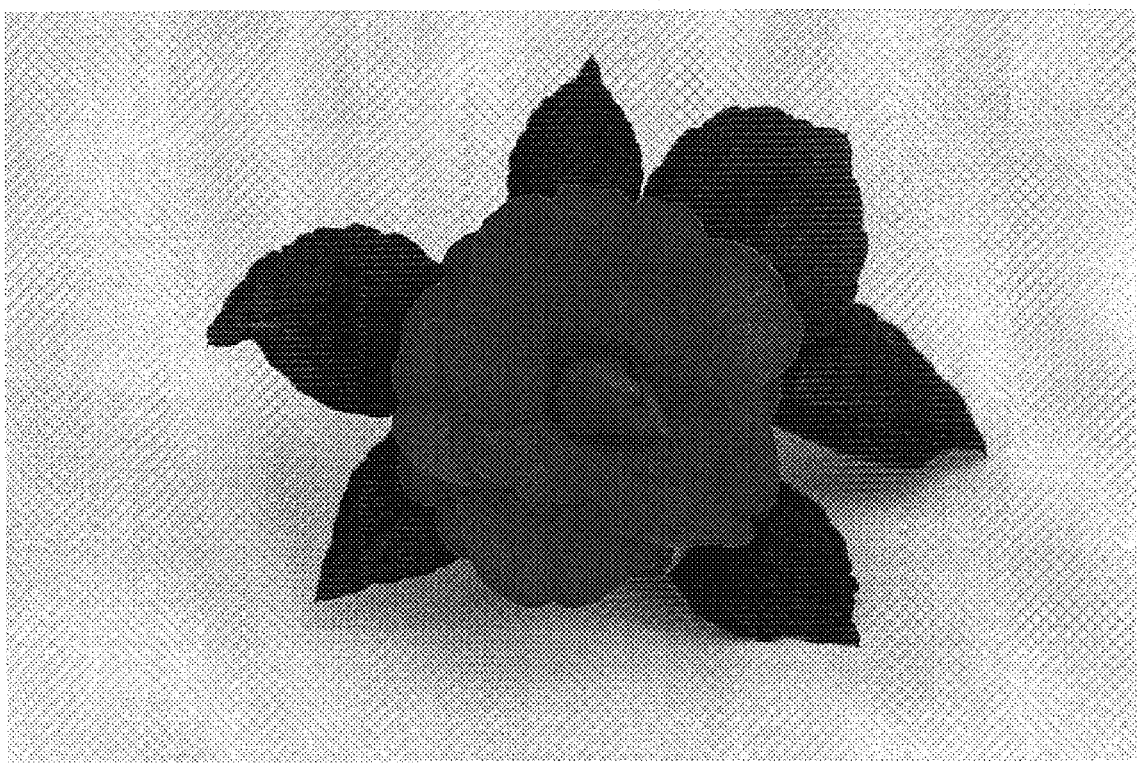

FIG. 2 illustrates in full color a close up of a typical bloom of 'DANMU24.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANMU24' plants grown in a greenhouse in Moshav Mishmar Hashiva, Israel. The growing temperature ranged from 20° C. to 25° C. during the day and 18° C. to 20° C. at night. The greenhouse is un-shaded, giving bright, normal sunlight conditions. Measurements and numerical values represent averages of typical plant types.

Botanical classification: *Impatiens walleriana* cultivar 'DANMU24.'

PROPAGATION

Time to initiate roots:
- *Summer.*—About 7 to 10 days at approximately 25° C.
- *Winter.*—About 10 to 15 days at approximately 21° C.

Root description: Fibrous, adventitious roots from cutting base.

Time to produce a rooted cutting:
- *Summer.*—About 15 to 18 days at approximately 25° C.
- *Winter.*—About 18 to 21 days at approximately 21° C.

PLANT

Growth habit: Compact, upright and rounded annual.
Pot size of plant described: 12 cm.
Height: Approximately 13 to 15 cm.
Plant spread: Approximately 35 cm.
Branching characteristics: Very free branching.
Length of primary lateral brances: Approximately 14 cm.
Diameter of lateral branches: Approximately 0.3 cm.
Quantity of lateral branches: Approximately 20 to 25.
Stem:
- *Form.*—Round in cross-section.
- *Color.*—Near RHS Green 193A., presence of red pattern on the internodes.
- *Texture.*—Smooth.
- *Strength.*—Very strong.

Internode length: Approximately 0.25 cm.
Age of plant described: Approximately 8 weeks from a rooted cutting.

FOLIAGE

Leaf:
- *Arrangement.*—Alternate.
- *Quantity.*—Approximately 32 per main branch.
- *Average length.*—Approximately 4.5 cm.
- *Average width.*—Approximately 2.5 cm.
- *Shape of blade.*—Ovate.
- *Apex.*—Acute.
- *Base.*—Acute.
- *Margin.*—Serrulate.
- *Texture of top surface.*—Smooth.
- *Texture of lower surface.*—Smooth.
- *Color.*—Young foliage upper side: Near RHS Green 138C. Young foliage under side: Near RHS Green 138B. Mature foliage upper side: Near RHS Green 138C. Mature foliage under side: Near RHS Green 138B.
- *Venation.*—Type: Pinnate. Pattern: Midrib with secondary veins on the abaxial side with no prominent veins on the adaxial side. Venation color upper side: Near RHS Green 137A. Venation color under side: Near RHS Green 138B.
- *Petiole.*—Length: About 1.0 to 1.5 cm. Diameter: About 0.1 cm. Texture: Smooth. Color upper surface: Near RHS Yellow-Green 145D. Color lower surface: Near RHS Yellow-Green 145D.

FLOWER

*Type and habit.*—Round, double flowers.
*Position.*—Raised above the foliage.
*Quantity per lateral branch.*—About 15 flowers and buds together per stem.
*Lastingness on the plant.*—About 10 days.
*Fragrance.*—None.
*Flowering season.*—Spring until fall in outdoor conditions.
*Flower diameter.*—About 4.0 to 4.5 cm.
*Flower depth* (*height*).—About 1 cm.

Buds:
- *Rate of opening.*—About 3 to 4 days.
- *Length.*—About 1.5 cm.
- *Diameter.*—About 1 cm.
- *Shape.*—Rounded.
- *Color* (*just before opening*).—Near RHS Red 41C.

Petals:
- *Quantity.*—About 25 to 50.
- *Arrangement.*—Imbricate.
- *Length.*—About 2 cm.
- *Width.*—About 1.5 cm.
- *Shape.*—Obcordate.
- *Apex.*—Retuse.
- *Base.*—Acute.
- *Margin.*—Entire.
- *Texture, upper and lower surfaces.*—Smooth. Color: When opening, upper surface: Near RHS Red 40C. When opening, lower surface: Near RHS Red 41D. Fully opened, upper surface: Near RHS Red 40C. Fully opened, lower surface: Near RHS Red 41D.

Spurs:
- *Quantity.*—One per flower.
- *Length.*—About 2.5 cm.
- *Diameter.*—About 0.1 cm.
- *Aspect.*—Spur curvature 40°–45° from peduncle.
- *Color.*—Towards base: Near RHS Yellow-Green 145C. Apex: Near RHS Greyed-Red 182A.

Sepals:
- *Quantity.*—2.
- *Length.*—About 1.0 to 1.3 cm.
- *Width.*—About 0.7 to1.0 cm.
- *Shape* (*overall*).—Oblong. Apex: Rounded. Base: Rounded.
- *Margin.*—Entire.
- *Color.*—Near RHS Yellow-Green 149D.

Peduncles:
- *Length.*—About 2.0 cm.
- *Diameter.*—About 0.1 cm.
- *Angle.*—About 45° to the lateral branch.
- *Strength.*—Stable, flexible.
- *Texture.*—Smooth.
- *Color.*—Near RHS Yellow-Green 145C.

REPRODUCTIVE ORGANS

Sterile, no reproductive organs.

OTHER CHARACTERISTICS

Seeds and fruits: Not present, sterile.

Disease/pest resistance: Neither resistance nor susceptibility to pathogens and pests common to *Impatiens* have been observed.

Temperature tolerance: Sensitive to temperatures below 10° C.

What is claimed is:

1. A new and distinct cultivar of *Impatiens* plant named 'DANMU24' as herein illustrated and described.

* * * * *